US006467333B2

(12) United States Patent
Lewis et al.

(10) Patent No.: US 6,467,333 B2
(45) Date of Patent: Oct. 22, 2002

(54) TRACE LEVEL DETECTION OF ANALYTES USING ARTIFICIAL OLFACTOMETRY

(75) Inventors: Nathan S. Lewis, La Canada; Erik J. Severin, San Marino; Bernard Wong, Los Angeles, all of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/815,618

(22) Filed: Mar. 22, 2001

(65) Prior Publication Data

US 2002/0017125 A1 Feb. 14, 2002

Related U.S. Application Data

(63) Continuation of application No. 09/335,425, filed on Jun. 17, 1999, now Pat. No. 6,244,096.
(60) Provisional application No. 60/091,179, filed on Jun. 30, 1998, and provisional application No. 60/090,012, filed on Jun. 19, 1998.

(51) Int. Cl.[7] ................. A61B 19/00; A61B 5/08; G01N 29/00; G01N 31/06; G01N 27/12

(52) U.S. Cl. ............. 73/31.05; 73/23.3; 73/61.41; 422/84; 422/88; 600/530; 600/532

(58) Field of Search ............... 73/31.05, 23.2, 73/23.3, 23.34, 61.41, 53.01; 422/84, 88, 78, 101; 600/530, 531, 532

(56) References Cited

U.S. PATENT DOCUMENTS

| | | | |
|---|---|---|---|
| 3,897,679 A | 8/1975 | Guild | 73/61.1 |
| 4,381,922 A | 5/1983 | Frey et al. | 422/98 |
| 4,457,161 A | * 7/1984 | Iwanaga et al. | 73/23 |
| 4,670,405 A | 6/1987 | Stetter et al. | 436/151 |
| 4,718,268 A | 1/1988 | Reid et al. | 73/23 |
| 4,749,553 A | 6/1988 | Lopez et al. | 422/84 |
| 4,759,210 A | 7/1988 | Wohltjen | 73/23 |
| 4,818,348 A | 4/1989 | Stetter | 204/1 T |
| 4,822,465 A | * 4/1989 | Jones et al. | 204/192.1 |
| 5,025,653 A | 6/1991 | Schuldt | 73/1 G |
| 5,248,617 A | 9/1993 | DeHann | 436/137 |
| 5,265,463 A | 11/1993 | Loebig | 73/38 |
| 5,269,169 A | 12/1993 | Trenkle | 73/23.34 |

(List continued on next page.)

FOREIGN PATENT DOCUMENTS

| | | | |
|---|---|---|---|
| WO | WO 94/04916 | 3/1994 | |
| WO | WO 9607901 | 3/1996 | ......... G01N/33/00 |
| WO | WO 97/08337 | 3/1997 | |
| WO | WO 98/29563 | 7/1998 | ............ C12Q/1/04 |
| WO | WO 98/36272 | 8/1998 | ......... G01N/33/00 |
| WO | WO 98/39409 | 9/1998 | ............ C12M/1/34 |
| WO | WO 98/39470 | 9/1998 | ............ C12Q/1/04 |
| WO | WO 99/09407 | 2/1999 | ......... G01N/31/22 |
| WO | WO 99/09408 | 2/1999 | ......... G01N/31/22 |
| WO | WO 00/11209 | 3/2000 | |
| WO | WO 00/32091 | 6/2000 | |
| WO | WO 00/54050 | 9/2000 | |

OTHER PUBLICATIONS

Greenfield, P. "AromaScan sniffs out medical applications." *Clinica*, May 23, 1994, pp. 20–21.

Primary Examiner—Herzon Williams
Assistant Examiner—David J. Wiggins
(74) Attorney, Agent, or Firm—Townsend and Townsend and Crew, LLP

(57) ABSTRACT

The present invention provides a device for detecting the presence of an analyte, such as for example, a lightweight device, including: a sample chamber having a fluid inlet port for the influx of the analyte; a fluid concentrator in flow communication with the sample chamber wherein the fluid concentrator has an absorbent material capable of absorbing the analyte and capable of desorbing a concentrated analyte; and an array of sensors in fluid communication with the concentrated analyte to be released from the fluid concentrator.

45 Claims, 8 Drawing Sheets

U.S. PATENT DOCUMENTS

| | | |
|---|---|---|
| 5,325,705 A | 7/1994 | Tom ........................... 73/31.03 |
| 5,369,978 A | 12/1994 | Mookherjee et al. ....... 73/23.34 |
| 5,383,469 A * | 1/1995 | Vreman et al. ............. 128/719 |
| 5,469,369 A | 11/1995 | Rose-Pehrsson et al. ... 364/497 |
| 5,479,815 A | 1/1996 | White et al. ................. 73/23.3 |
| 5,501,231 A * | 3/1996 | Kaish .......................... 128/725 |
| 5,522,918 A | 6/1996 | Shiramizu ...................... 95/87 |
| 5,546,931 A | 8/1996 | Rusz ..................... 128/203.12 |
| 5,571,401 A | 11/1996 | Lewis et al. ................. 205/787 |
| 5,585,575 A | 12/1996 | Corrigan et al. ......... 73/863.71 |
| 5,621,162 A | 4/1997 | Yun et al. ................... 73/23.34 |
| 5,739,412 A | 4/1998 | Stock et al. ................. 73/23.3 |
| 5,787,885 A | 8/1998 | Lemelson .................... 128/632 |
| 5,801,297 A * | 9/1998 | Mifsud et al. ............. 73/23.34 |
| 5,807,701 A | 9/1998 | Payne et al. .................. 435/34 |
| 5,814,474 A | 9/1998 | Berndt ........................ 435/34 |
| 5,814,524 A | 9/1998 | Walt et al. .................. 436/518 |
| 5,815,524 A | 9/1998 | Walt et al. .................. 436/518 |
| 5,891,398 A | 4/1999 | Lewis et al. .............. 422/82.02 |
| 5,962,335 A * | 10/1999 | Katzman ..................... 436/181 |
| 5,965,803 A | 10/1999 | Chin, Jr. et al. ........... 73/23.34 |
| 5,971,937 A * | 10/1999 | Ekström ..................... 600/532 |
| 6,057,162 A | 5/2000 | Rounbehier et al. ........ 436/119 |
| 6,067,989 A * | 5/2000 | Katzman .................... 128/898 |
| 6,099,480 A * | 8/2000 | Gustafsson ................. 600/532 |
| 6,129,680 A * | 10/2000 | Mottram .................... 600/532 |
| 6,170,318 B1 | 1/2001 | Lewis ................... 0763/23.34 |
| 6,319,724 B1 | 1/2001 | Lewis et al. ................ 436/149 |
| 6,244,096 B1 | 6/2001 | Lewis et al. ............... 073/23.2 |
| 6,248,078 B1 * | 6/2001 | Risby et al. ................ 600/529 |

* cited by examiner

TRACE LEVEL DETECTION OF ANALYTES USING ARTIFICIAL OLFACTOMETRY

CROSS-REFERENCES TO RELATED APPLICATIONS

The present application is a continuation of U.S. patent application No. 09/335,425, filed Jun. 17, 1999, now U.S. Pat. No. 6,244,096, which claims priority to U.S. Provisional Applications Ser. No. 60/090,012, filed Jun. 19, 1998, and 60/091,179, filed Jun. 30, 1998, the disclosures of which are incorporated herein by reference in their entirety.

STATEMENT AS TO RIGHTS TO INVENTIONS MADE UNDER FEDERALLY SPONSORED RESEARCH AND DEVELOPMENT

The research carried out in the subject application was sponsored, in part, by grants from: ARO (DAAG-55-97-1-0187); DARPA (DAAK60-97-K-9503); and NASA (49-244-30002-0-8280), and is subject to the provisions of Public Law 96-517 (35 U.S.C. § 202). The government may have certain rights in any patents issuing on this application.

BACKGROUND OF THE INVENTION

An artificial olfactory system is a device that is capable of detecting a wide variety of analytes in fluids such as vapors, gases and liquids. The device comprises an array of sensors that in the presence of an analyte produces a response. The device produces a unique signature output for a particular analyte. Using pattern recognition algorithms, the output signature, such as an electrical response, can be correlated and compared to a particular analyte or mixture of substances that are known. By comparing the unknown signature with the stored or known signatures, the analyte can be detected, identified and quantified.

There are many instances where it is desirable to measure trace amounts of analytes. However, in certain instances, the analytes are found at levels that are too low to register a robust signal by direct exposure to currently available sensors. In headspace analysis of applications in agricultural, wine, tobacco, perfume, plastics, and the food industries, the detection and classification of trace levels of gases are present in the sub part per million (ppm) range, making detection difficult. Moreover, in residue analysis of pesticides on crops, the trace levels of certain herbicides must meet federal guidelines. For certain crops, these residues are present on the crops in the part per billion levels (ppb).

Another potential application wherein the detection of trace levels of analytes is important is the diagnosis of patients conditions from an analysis of their breath. Marker gases such as hydrogen sulfide and methyl mercaptan, which are important in diagnosing the presence of oral or lung conditions from the breath of human patients, often exist in concentrations of 0.01–1 parts per million (or lower). However, the threshold detection levels of currently known sensors are in the range of 1–100 parts per million.

Currently, the most widely used device for detecting oral malodors is the Halimeter, which is commercially available from Interscan Corp. (Chatsworth, Calif.). Using an electrochemical cell that is sensitive to volatile sulfur compounds (VSC), the device can oxidize the VSC at the anode according to the following reactions:

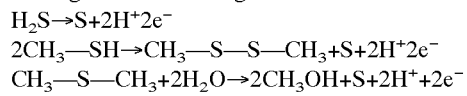

However, one obvious drawback is that the Halimeter cannot distinguish between volatile sulfur compounds. Similarly, other volatile substances can interfere with the readings of the VSC.

A second device for the detection of breath and odors associated therewith is based on zinc-oxide thin film semiconductor technology and has recently been developed for measuring VSC (see, Shimura M et al., *J. Periodontol.* 67:396–402 (1994)). New Cosmos Electric Co. (Osaka, Japan) manufactures this device. This device, however, is limited because it is susceptible to interference from organic vapors unrelated to oral malodor (see, Yaegaki K, In Rosenberg, "Bad Breath: Research Perspectives," *Proceedings of the First International Workshop on Oral Malodor*, Ramot Publishing, Tel Aviv University pp. 41–54 (1993)) 87–108 (1995)).

Another analysis for breath detection is a test based on the enzyme substrate benzoyl-DL-arginine-naphthylamine (BANA) (see, Loesche et al., *J. Clin. Microbiol.* 28:1551–1559 (1991); and Loesche etal. *J. Periodontol.*, 61:189–196 (1991)). This test is marketed -under the brand name Peroscan and is available from Oral-B Laboratories (Redwood City, Calif.). Scrapings from the tongue, saliva, or plaque samples are deposited directly on a reagent card. Following substrate addition, a blue spot develops if anaerobes are present. Studies have shown that BANA results are not highly correlated with VSC measurements and that the test is often detecting other analytes (see, Kozlovsky et al., *J. Dent. Res.*, 73:1036–1042 (1994)).

It has been estimated that at least 50% of the population suffers from chronic oral malodor (see, Bosy, *J. Can. Dent. Assoc.* 63:196–201 (1997)). A significant fraction of the population is worried about bad breath, even though there is usually no underlying disease (see, Iwakura et al., *J. Dent. Res.* 7:1568–1574 1 (1994)). Food, of course, is another cause of oral malodors. However, there are many people who have an unwarranted phobia of bad breath. The size of the market for breath fresheners, chewing gums, and mouth rinses is an indicator of this propensity.

In addition to mammalian breath measurements, respiratory devices for anesthetic and respiratory gas mixtures must be monitored at very low concentrations of analytes. Medical devices mix the anesthetic with breathing gas prior to delivery to the patient. In an anesthetic device, it is imperative that the concentration of the anesthetic, gas flow and amounts of the mixture and starting gases be known with certainty. In most instances, the anesthetic amounts are at very low concentration levels.

One approach to increase sensitivity to certain analytes is to use selective filters or membranes. For instance, U.S. Pat. No. 5,841,021, which issued to De Castro et al., discloses an electrochemical gas sensor that has a catalytically active sensor electrode, a reference electrode and a permselective filter or membrane layer. The filter is made of a material that provides for molecular specificity of certain gases, such as carbon monoxide. The membrane allows the sensors to be selective to the chemical analyte of interest. The filter only allows the analytes of interest to contact the sensor. By removing interfering substances through filtration, the sensor becomes more selective and thus sensitive to the analyte of interest.

In addition, U.S. Pat. No. 5,057,436, which issued to Ball, discloses a method and apparatus for detection of toxic gases, such as ammonia, using a metal oxide semiconductor and an electrochemical sensor. Disposed between the two sensors is an absorber having an absorbent that reacts with ammonia.

In view of the foregoing, what is needed in the art is a vapor concentrator for an array of sensors, especially for an electronic nose sensor array. In addition, methods are needed to detect odors and diagnose medical conditions. The present invention fulfills these and other needs.

SUMMARY OF THE INVENTION

In certain instances, it is desirable to measure trace amounts of analytes using sensor array technology. The present invention increases the sensitivity to such analytes by a large factor, and thus allows for the use of existing sensor systems for applications where an increase in sensitivity renders them more effective. As such, in certain aspects, the present invention provides a device for detecting the presence of an analyte, the device comprising: a sample chamber having a fluid inlet port for the influx of the analyte; a fluid concentrator in flow communication with the sample chamber, wherein the fluid concentrator has an absorbent material capable of absorbing the analyte and capable of desorbing a concentrated analyte; and an array of sensors in fluid communication with the concentrated analyte. In certain preferred embodiments, the device further includes a detector operatively associated with each sensor that provides a response in the presence of the analyte.

The absorbent material of the fluid concentrator can be, but is not limited to, a nanoporous material, a microporous material, a chemically reactive material, a nonporous material and combinations thereof In certain instances, the absorbent material can concentrate the analyte by a factor that exceeds a factor of about $10^5$, and more preferably by a factor of about $10^2$ to about $10^4$. Using the device of the present invention, the analyte can be concentrated from an initial sample volume of about 10 liters and then desorbed into a concentrated volume of about 10 milliliters or less, before being presented to the sensor array.

In another embodiment, removal of background water vapor is conducted in conjunction, such as concomitantly, with the concentration of the analyte. Once the analyte is concentrated, it can be desorbed using a variety of techniques, such as heating, purging, stripping, pressuring or a combination thereof.

In yet another aspect, the present invention provides methods for detecting or diagnosing, for example, infections, lung cancer, oral infections and halitosis using a breath sample of a mammal. Preferably, the mammal is a human being. In other embodiments, the present invention provides methods for other medical applications, such as those involving the detection of marker gas(es) in mammalian breath as well as odors from potentially infected areas of the skin.

In still yet another aspect, the present invention provides methods and devices for the process control of anesthetic gases of clinical interest. Using the apparatus of the present invention, monitoring and quantitating anesthetics is readily accomplished.

These and other embodiments and advantages will be readily apparent when read with the accompany drawings and the detailed description of the invention which follows.

DETAILED DESCRIPTION OF THE INVENTION AND PREFERRED EMBODIMENTS

I. The Device

In one aspect, the present invention allows existing sensor systems to be more effective and efficient by providing enhancements in the detection sensitivity to trace analytes. As such, in one embodiment, the present invention provides a device for detecting the presence of an analyte in a fluid, comprising:

a) a sample chamber having a fluid inlet port for the influx of the analyte;

b) a fluid concentrator in flow communication with the sample chamber, the fluid concentrator having an absorbent material capable of absorbing the analyte and capable of desorbing a concentrated analyte; and c) an array of sensors in fluid communication with the concentrated analyte.

In preferred embodiments, the device further comprising a detector operatively associated with each sensor that provides a response in the presence of an analyte. In certain embodiments, the sample chamber is designed for the collection of mammalian breath. Under certain conditions, mammalian breath contains marker gases indicative of certain infections, disorders and medical conditions and the devices of the present invention can be used to detect such marker gases. In certain aspects, the sample chamber is a breath collector and concentrator (BCC) and is fabricated to collect the breath of a mammal. Preferably, the mammal is a human being, although the BCC can be fabricated to collect the breath of other mammals such as cows, sheep, horses, dogs, cats, hogs, etc. The BCC is convenient to use and in certain instances is a portable handheld device with a suitable handle portion for convenient use.

Figure 1:
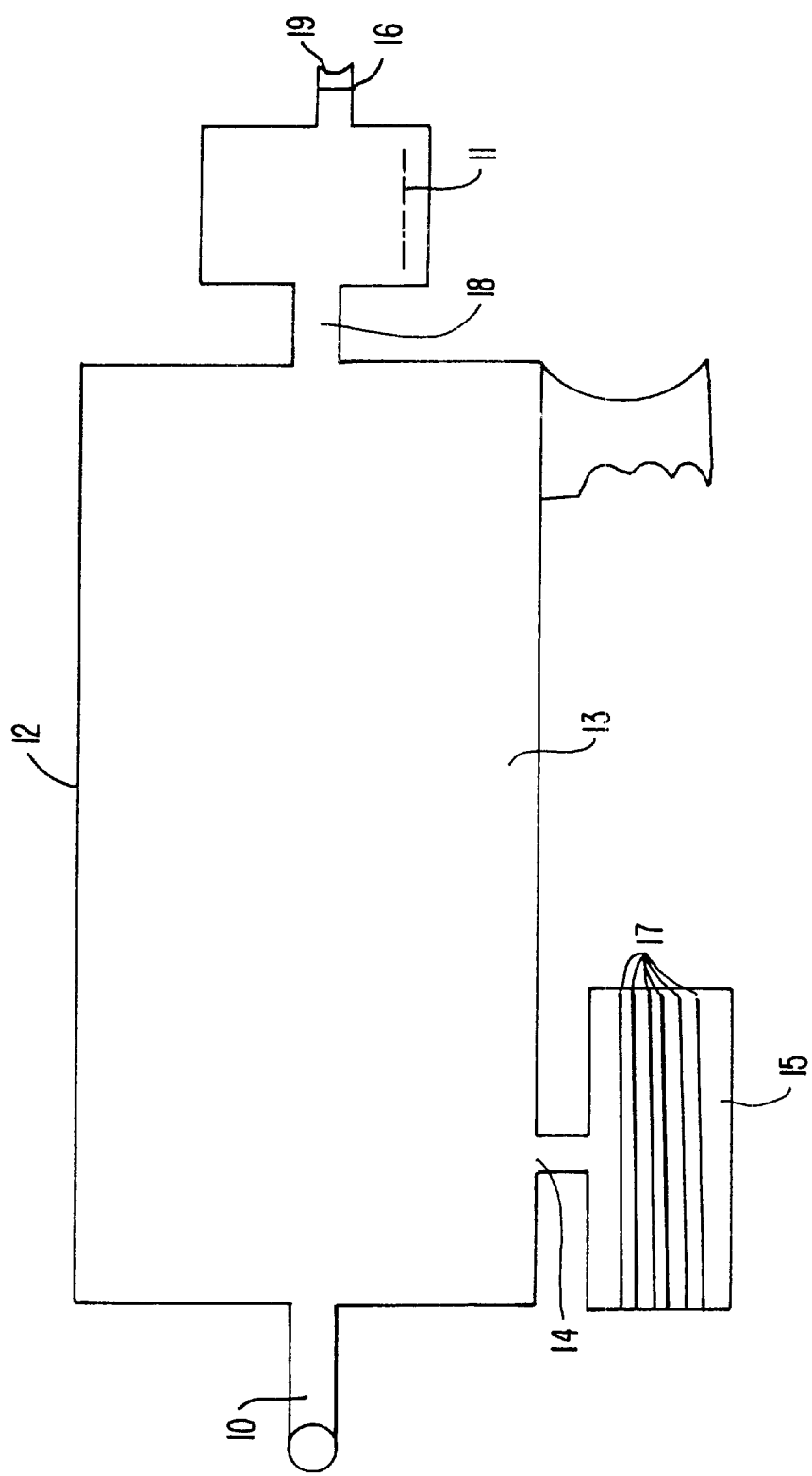
FIG. 1 is a cross-sectional view of a breath collector and concentrator of the present invention.

With reference to FIG. 1, in certain embodiments, the sample chamber is a cylindrical reservoir having an inlet port (10) for the influx of gas, such as breath, and an outlet port (19) for the exhaust of breath The BCC has a first end and a second end. The cylindrical container (12) extends between the first end and the second end, and the cylindrical container has an open interior chamber (13).

The first end of the body is open for access to the interior chamber and functions as a breath inlet port and is vented by a breath exhaust. The breath inlet port optionally contains a disposable adapter for multiple use. A concentrator portal (14) opens into the interior chamber and is in flow communication with the fluid concentrator. The fluid concentrator (15) comprises an absorbent material capable of absorbing the analyte and capable of desorbing a concentrated analyte. In certain embodiments, valves control the breath flow so the sample of breath within the chamber can be directed to the fluid concentrator. The fluid concentrator optionally contains a second exhaust or exit port.

A valve (16) is mounted anterior to the outlet port with sufficient force to maintain the vent closed except when the mammal is exhaling into the chamber. Optionally, the fluid concentrator is jacketed (17) with a heater for the purpose of desorbing a concentrated analyte. As illustrated in FIG. 1, the BCC has a sensor array portal (18) that opens into the interior chamber and is in fluid communication with the desorbed concentrated analyte and the sensor array (11). In certain embodiments, the sensor array is disposed downstream of the inlet port and the concentrator portal. In other embodiments, the sensor array is disposed between the inlet port and the concentrator portal (not shown). In certain embodiments, the BCC has an adapter to provide breath from the nostril(s) to avoid cross-contamination from the mouth.

Figure 2:
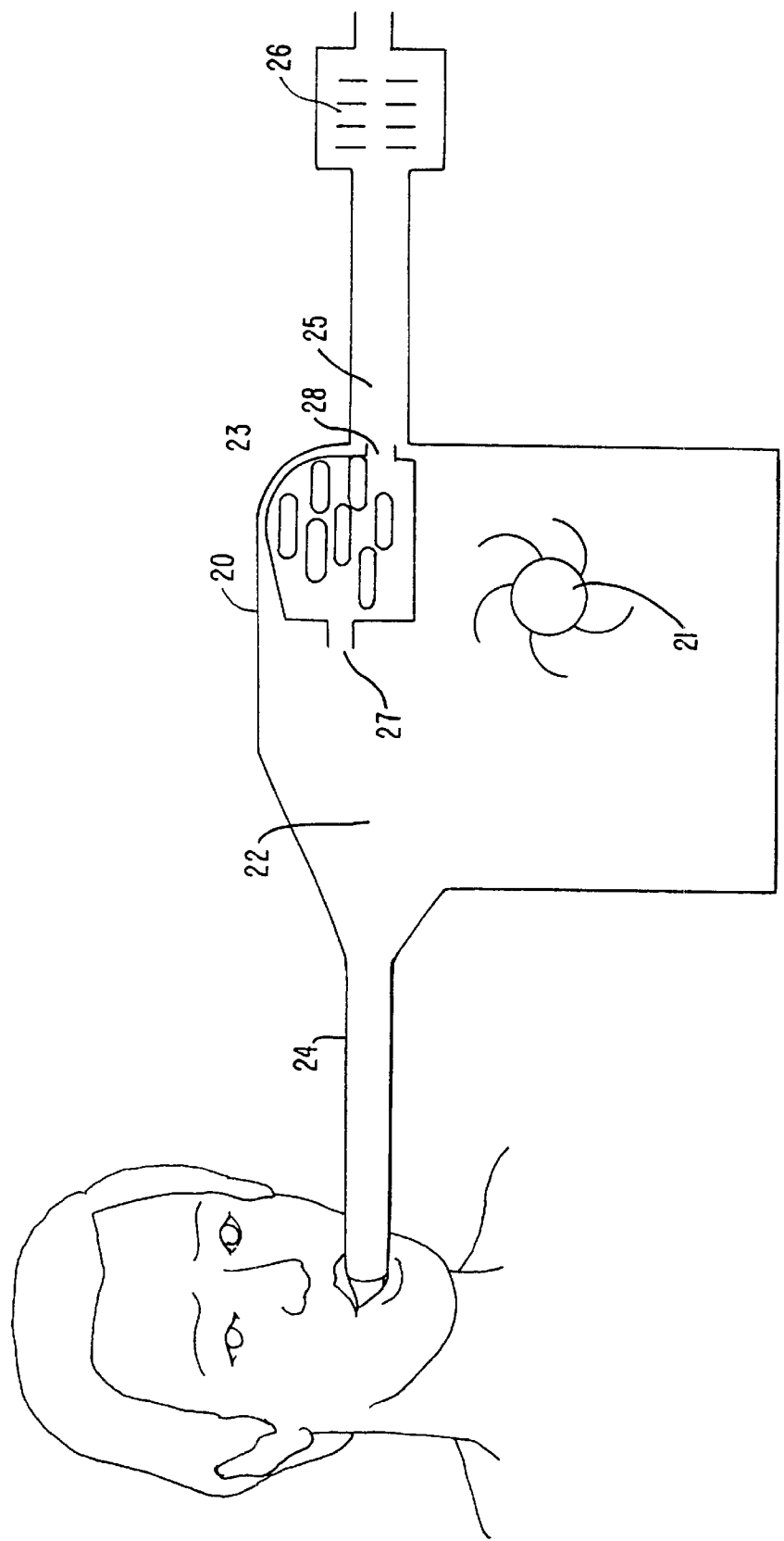
FIG. 2 is a cross-sectional view of a breath collector and concentrator of the present invention.

In certain aspects, the BCC can be a desktop model. As illustrated in FIG. 2, the first end (24) of the BCC (20) is open for access to the interior chamber (22) and functions as a breath inlet port and is vented by a breath exhaust (25). A fluid concentrator (23) opens into the interior chamber (27) and is in flow communication (28) with the breath exhaust (25). In this embodiment, the breath is circulated through the chamber using a fan (21). The sensor array (26) is in flow communication with the desorbed analyte.

In various embodiments, the fluid concentrator can be disposed within the sample chamber or outside the sample chamber. In addition, the sensor array can be disposed within the sample chamber or outside the sample chamber. Moreover, the sensor array can be configured to be external from the BCC and to extend into the mouth. or nasal cavity. The present invention embodies all such variations.

Although the device of FIG. 1 is shown as a handheld breath collector and concentrator, those of skill in the art will appreciate that in certain other embodiments, the device and methods of the present invention can be adapted and configured to detect within or around various other areas of interest including, but not limited to, mucous membranes, nose, nasal passages, eye, skin, ear, inner ear, mouth, tongue, throat, colon, duodenum, body cavities, stomach, vagina and penis. Moreover, the device and methods of the present invention can be configured to detect all body fluids including, but not limited to, urine, perspiration, tears, blood, mucus, pus, salvia, feces, menstruation fluid, sperm, eggs, spinal fluid and mammary gland discharge.

Figure 3:
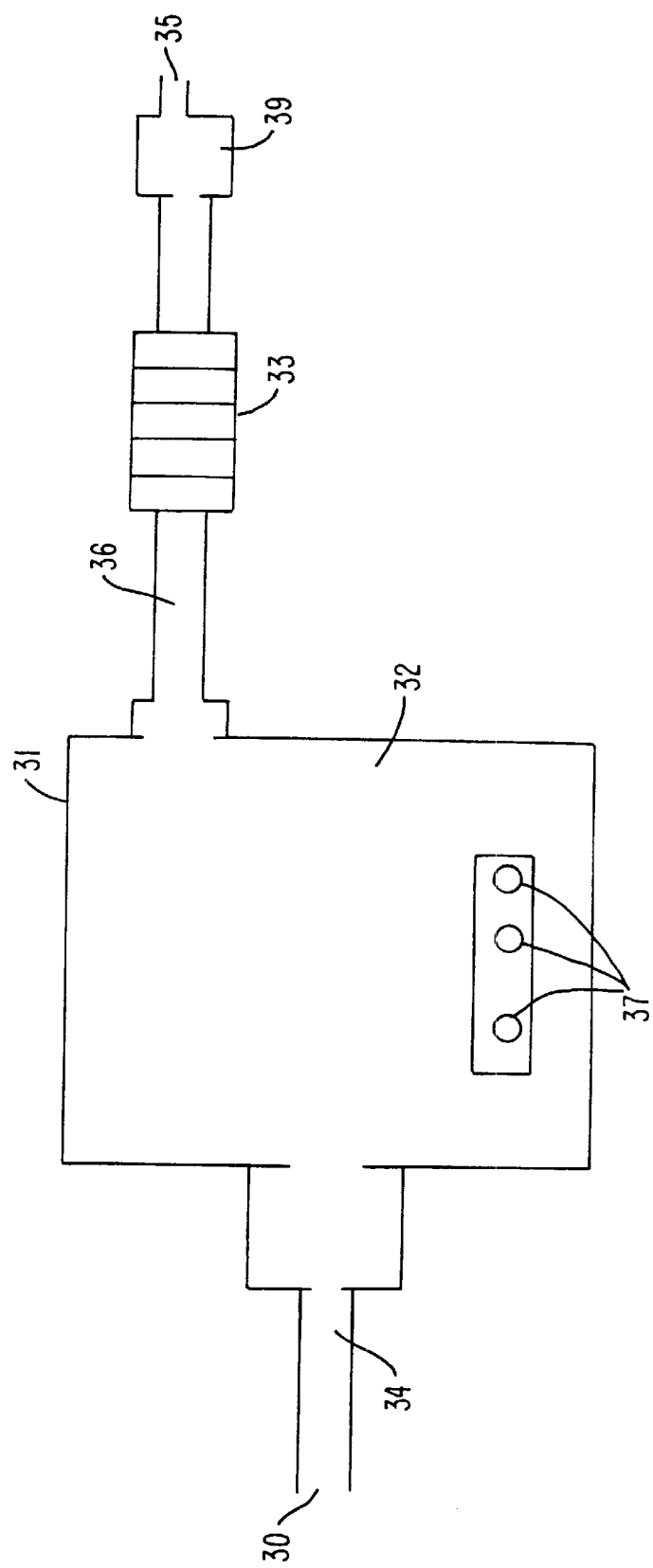
FIG. 3 is a head space analyzer of the present invention.

In another embodiment, the sample chamber is a head space analyzer (HSA) and can be fabricated from an inert material, such as a molded fiberglass, or in certain embodiments can be fabricated from plastic and can be configured like a box. As illustrated in FIG. 3, the sample chamber (32) optionally has a glass-viewing window and the box can contain pressure and temperature gauges (37) to allow pressure and temperature monitoring. Moreover, the sample chamber optionally contains valves for gas input and exhaust of the box. Optionally, the sample chamber comprises a heater and a pressure control means for an internally controlled atmosphere.

Similar to the BCC, the HSA has a first end (34) that is open for access to the interior chamber (32) and functions as an inlet port (30) and is vented by an exhaust (35). A fluid concentrator (33) is disposed outside the sample chamber and is in flow communication (36) with the exhaust (35). The sensor array (39) is in flow communication with the desorbed analyte.

Optionally, the HSA contains appropriate connections for high throughput screening (HTS). High throughput screening includes a robotic armature system. In general, these systems include automated workstations like the automated apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.), which mimic the manual operations performed by a technician. The nature and implementation of modifications to these devices (if any) so that they can operate will be apparent to persons skilled in the relevant art.

In operation, a volume of the gas to be sampled, such as human breath, is introduced into a sample chamber where it is transported by means of convention into the vicinity of the sorbent material. Suitable transporting means include, but are not limited to, a fan, an air pump, or it can be means for heating the cylindrical container (12) to create a convective air flow between the inlet and the outlet. The sorbent material is chosen from known materials designed for the purpose of sorbing gases, vapors, and the like. In certain embodiments, the sorbent material includes, but is not limited to, a nanoporous material, a microporous material, a chemically reactive material, a nonporous material and combinations thereof. Such absorbents include, for example, activated carbon, silica gel, activated alumina, molecular sieve carbon, molecular sieve zeolites, silicalite, $AlPO_4$, a polymer, a co-polymer, alumina and mixtures thereof In certain embodiments, the absorbent has a pore size from about 1 nm to about 100 nm and, preferably, from about 1 nm to about 50 nm.

Suitable commercially available adsorbent materials are disclosed in U.S. Patent Application Ser. No. 09/271,873, filed Mar. 18, 1999, and include, but are not limited to, Tenax TA, Tenax GR, Carbotrap, Carbopack B and C, Carbotrap C, Carboxen, Carbosieve SIII, Porapak, Spherocarb, and combinations thereof Preferred adsorbent combinations include, but are not limited to, Tenax GR and Carbopack B; Carbopack B and Carbosieve SIII; and Carbopack C and Carbopack B and Carbosieve SIII or Carboxen 1000. Those skilled in the art will know of other suitable absorbent materials.

After sometime period that is chosen to be adequate for sorbing the desired analytes from the vapor phase onto the material, the circulation is stopped and then the material is desorbed from the sorbent phase and released into the sensor chamber. The desorbing of the concentrated analyte for the sorbent can be by accomplished by thermal means, mechanical means or a combination thereof Desorption methods include, but are not limited to, heating, purging, stripping, pressuring or a combination thereof.

In certain embodiments, the sample concentrator is wrapped with a wire through which current can be applied to heat and thus, desorb the concentrated analyte. The analyte is thereafter transferred to the sensor array.

The process of sorbing the material onto the sorbent phase not only can be used to concentrate the material, but also can be advantageously used to remove water vapor. The water vapor is preferably removed prior to concentrating the analyte; however, in various embodiments, the vapor can be removed concomitantly or after the analyte is concentrated. In a preferred embodiment, the water vapor is removed prior to presenting the desired analyte gas mixture to the sensor array. Thus, in certain embodiments, the fluid concentrator contains additional absorbent material to not only concentrate the analyte, but to remove unwanted materials such gas contaminates and moisture.

In certain instances and depending on the absorbent used, the concentration factor can exceed a factor of $10^5$, and more preferably by a factor of about $10^2$ to about $10^4$. Thus, the analyte gases can be concentrated from an initial sample volume of about 10 liters and then desorbed into a volume of about 10 milliliters or less when they are presented to the sensor array.

The array of sensors is present in fluid communication with the concentrated analyte. Various sensors suitable for detection of analytes include, but are not limited to: surface acoustic wave (SAW) sensors; quartz microbalance sensors; conductive composites, chemiresitors; metal oxide gas sensors, such as tin oxide gas sensors; organic gas sensors; metal oxide field effect transistor (MOSFET); piezoelectric devices; infrared sensors, temperature sensors, humidity sensors, sintered metal oxide sensors; Pd-gate MOSFET; metal FET structures; metal oxide sensors, such as a Tuguchi gas sensors; phthalocyanine sensors; electrochemical cells; conducting polymer sensors; catalytic gas sensors; organic semiconducting gas sensors; solid electrolyte gas sensors; piezoelectric quartz crystal sensors; dye-impregnated polymer films on fiber optic detectors; polymer-coated micromirrors; electrochemical gas detectors; chemically sensitive field-effect transistors; carbon black-polymer composite chemiresistors; micro-electromechanical system devices; and micro-opto-electro-mechanical system devices and Langmuir-Blodgett film sensors.

In a preferred embodiment, the sensors used in the present invention are disclosed in U.S. Pat. No. 5,571,401, which is incorporated herein by reference. Briefly, the sensors described therein are conducting materials and nonconducting materials arranged in a matrix of conducting and non-conducting regions. The nonconductive material can be a nonconducting polymer such as polystyrene. The conductive material can be a conducting polymer, carbon black, an inorganic conductor and the like. The sensor arrays comprise at least two sensors, typically about 32 sensors, and in certain instances 1000 or more sensors up to about $10^6$ sensors. In a preferred embodiment, at least two sensors are compositionally different. The array of sensors can be formed on an integrated circuit using semiconductor technology methods, an example of which is disclosed in PCT Patent Publication No. WO99/08105, entitled "Techniques and Systems for Analyte Detection," published Feb. 19, 1999, and incorporate herein by reference. Another preferred sensor system is disclosed in PCT Patent Publication No. WO99/27357, published Jun. 6, 1999.

In certain embodiments, the temporal response of each sensor (response as a function of time) is recorded and can be displayed. Various responses include, but are not limited to, resistance, impedance, capacitance, inductance, magnetic, optical, etc. The temporal response of each sensor can be normalized to a maximum percent increase and percent decrease that produces a response pattern associated with the exposure of the analyte. By iterative profiling of known analytes, a structure-function database correlating analytes and response profiles is generated. Unknown analytes can then be characterized or identified using response pattern comparison and recognition algorithms. Accordingly, analyte detection systems comprising sensor arrays, a measuring device for detecting responses across each sensor, a computer, a display, a data structure of sensor array response profiles, and a comparison algorithm(s) or comparison tables are provided. In another embodiment, the electrical measuring device or detector is an integrated circuit comprising neural network-based hardware and a digital-analog converter (DAC) multiplexed to each sensor, or a plurality of DACs, each connected to different sensor(s).

In certain embodiments, a method for using the sensors for detecting the presence of an analyte in a fluid involves sensing the presence of an analyte in a fluid with a chemical sensor comprising first and second conductive leads electrically coupled to and separated by a chemically sensitive sensor as described above by measuring a first response between the conductive leads when the sensor is contacted with a first fluid comprising an analyte at a first concentration and a second different response when the sensor is contacted with a second fluid comprising the analyte at a second different concentration. As discussed above, suitable responses include, but are not limited to, resistance, impedance, capacitance, inductance, magnetic, optical, etc.

II. Medical Applications

The methods and apparatus of the present invention are extremely useful and can be advantageously used for the detection, identification, and classification of trace gas components, and are extremely useful in a variety of applications, including medical applications. In certain aspects, the methods and devices of the present invention are useful and very effective for the detection and diagnosis of diseases. In general, certain volatile marker gas(es) characterizes the detection or diagnosis of a disease state or medical condition. The methods and apparatus of the present invention can advantageously by used to detect volatile marker gases and compounds indicative of medical conditions, disease processes, infections, illness and well-being. Using these marker gases and compounds, clinicians can use the diagnostic instruments and methods of the present invention to make diagnoses and formulate appropriate treatments. The methods as described can optionally be performed using a fluid concentrator as described herein.

A. Oral infections

In certain aspects, the present invention is extremely useful for the detection of infections, such as oral infections and dental cares. For example, bacteria cause two widespread dental problems halitosis and periodontal disease and,: as disclosed herein, the methods and apparatus of the present invention can detect the off-gases produced by such bacteria.

1. Halitosis

Halitosis is caused by the breakdown of proteins by microbes on the back of the tongue. The tongue coating is comprised of epithelial cells from the oral mucosa, leukocytes from periodontal pockets, and microorganisms. While the mouth is resident to over 300 bacterial species (see, Loesche et al., In Rosenberg M., Editor, "Bad Breath: Research Perspectives," *Proceedings of the First International Workshop on Oral Malodor*, Ramot Publishing, Tel Aviv University pp. 41–54 (1993)), the relative size of each population is a function of many factors. Bad breath has been associated with the expansion of anaerobic species (see, Loesche et al., In Rosenberg Ed., "Bad Breath: Research Perspectives," *Proceedings of the First International Workshop on Oral Malodor*, Ramot Publishing, Tel Aviv University pp. 41–54 (1993); de Boveri HE et al., *J. Am. Dent. Assoc.*, 126:1384–1393 (1995)). The underlying cause of the increase in anaerobes can be poor oral hygiene, aging, deep crevices in the tongue, post-nasal drip, or numerous other conditions.

The chemical markers of bad breath have been identified and include, but 30 are not limited to, volatile sulfur compounds (VSC) (see, Richter et al, *Arch. Oral Biol.*, 9:47–53. (1964); Tonzetich, *Arch. Oral Biol.*, 16:587–597 (1971); Tonzetich, *J. Periodontol.* 48:13–20 (1977); Tonztich J, *J. Int. Dent. J.* 28:309–319 (1978); and Tonzetich, *Arch. Oral Biol.*, 16:587–597 (1971)).

As such, the present invention provides a method for the detection of halitosis, the method comprising: contacting an array of sensors with mammalian breath suspected of containing a marker gas indicative of halitosis; and detecting the marker gas to determine the presence of halitosis. In preferred embodiments, the marker gases being detected by the sensors are volatile sulfur compounds.

2. Periodontal Disease

A far more serious consequence of oral infections is periodontal disease. Gingivitis is the inflammation of the gums and periodontitis is when the gum infection damages the bone and supporting tissues. These conditions are the result of the expansion of certain species of bacteria. If a piece of food is trapped between the teeth, the bacterial types that can utilize the various nutrients present will multiply. In. addition, some of their metabolic products can give rise to a second array of organisms. And finally, if the population explosion of bacteria is sufficient to elicit an inflammatory response, a third wave of bacteria can arise that prefers the gingival crevicular fluid (see, Loesche W J et at, In Rosenberg, Bad Breath Research Perspectives, Ramot Publishing, Tel Aviv, pp. 41–54 (1993)).

VSC are also an indicator of periodontal disease (see, Loesche et al., In Rosenberg, Bad Breath: *Research Perspectives*, Ramat Publishing, Tel Aviv, (1995); Yaegaki et al., *J. Periodontia. Res.* 27:233–238 (1992); Tonzetich et al., *J. Dent. Res* 58:175 (1979); Frostell et al., *Dent. J.* 20:436–450 (1970), Sato et al., *Bull. Tokyo Dent. Coll.*, 21:171–178 (1980); Kostelc et al., *J. Periodontal Res.* 15:185–192 (1980)). In addition, a number of other compounds can be indicative of various bacterial populations (see, Bosy et al., *J. Periodontal* 65:37–46 (1994); McCulloch et al., In Rosenberg, *Bad Breath Research Perspectives*, Ramat Publishing, Tel Aviv, pp. 109–117 (1995)).

A significant development in recent years has been the use of anti-microbials to treat periodontitis instead of surgery. It has been shown that 80% of patients scheduled for surgery or extractions could be successfully treated with a course of metronidazole, doxycycline, or chlorhecidine. Overall, only about 10% of the teeth required the conventional surgery or extraction. Surprisingly, by using the apparatus of the present invention, it is possible to make a quick diagnosis, thereby alleviating unnecessary surgery.

As such, the methods and apparatus of the present invention can be used for the detection of periodontal disease. Thus, the present invention provides a method for the detection of periodontal disease, the method comprising: contacting an array of sensors with mammalian breath suspected of containing a marker gas indicative of periodontal disease; and detecting the marker gas to determine the presence of periodontal disease. As explained above, and detailed hereinbelow, numerous marker gases can be used to detect and evaluate the severity of periodontal disease.

B. Pneumonia Detection

In certain instances, it currently takes two to three days to culture the bacteria and determine whether the species that cause pneumonia are present. Often, rather than waiting for this determination, medical personnel prescribe broad-spectrum antibiotics. Unfortunately, this prophylactic procedure can promote the emergence of antibiotic-resistant strains.

The methods and devices of the present invention can alleviate the unnecessary prescribing of antibiotic(s) by providing rapid accurate detection and diagnosis of bacteria attributable to pneumonia. Thus, the present invention provides a method for the detection of pneumonia, the method comprising: contacting an array of sensors with mammalian breath suspected of containing a marker gases indicative of pneumonia; and detecting the marker gas to determine the presence of pneumonia.

C. Wound healing

One of the major reasons for slow healing wounds can be a high level of bacteria. Frequently, wound healing is largely undetected due to lack of tests for detecting microorganisms. Slow wound healing is a problem that effects more than a million people each year and costs billions of dollars to treat. Unfortunately, one of the standard techniques of wound assessment is to smell the exudate on the dressing. Nurses are advised to be aware of a "repulsive" odor that may be associated with necrotic tissue and "acrid or putrid" smells that are. associated with anaerobic bacteria.

However, these methods suffer from lack of specificity. While the absence of odor is indicative of a clean wound, the presence of odor does not necessarily signal an infection The switch in recent years to moisture-retaining "wet dressings" has further complicated the problem of wound assessment. Most dressings have strong odors, but often times the odor is due entirely to the materials in the dressings.

While there is a quantitative culture methodology that can be employed to eliminate human errors, it is very expensive and time consuming As such, it is only used routinely in burn centers where patients are in much more serious conditions. Advantageously, the present invention provides a method for diagnosing wound healing comprising: contacting the vapors associated with the wound with an array of sensors, thereby assessing the wound healing process.

D. Vaginitis

The vaginal discharge of women with bacterial vaginitis often has a prominent fishy odor. The presence of methylamine, isobutylamine, putrescine, cadaverine, histamine, tyramine, and phenethylamine are marker gases of vaginitis (see, Brand et al., *Obstetrics and Gynecology*, 68, 682–685 (1985)). Thus, the present invention provides a method for the detection of vaginitis, the method comprising: contacting an array of sensors with vaginal vapors or discharge suspected of containing a marker gas indicative of vaginitis; and detecting the marker gas to determine the presence of vaginitis.

E. Fertility

In yet another aspect, the present invention provides methods and apparatus for the detection of ovulation. The fertile period of a female mammal, such as a human being, can be detected by. measuring axillary secretions. The markers are androstenol and/or dehydroepiandrosterone sulfate. Thus, the present invention provides a method for detecting ovulation, the method comprising: contacting an array of sensors with vaginal vapor for the presence of a marker gas indicative of ovulation; and detecting the marker gas to determine ovulation.

F. Other Applications

In addition to the foregoing applications, other applications for the methods and devices of the present invention include, but are not limited to, environmental toxicology, remediation, biomedicine, material quality control, food monitoring, agricultural monitoring, heavy industrial manufacturing, ambient air monitoring, worker protection, emissions control, product quality testing, oil/gas petrochemical applications, combustible gas detection, $H_2S$ monitoring, hazardous leak detection, emergency response and law enforcement applications, explosives detection, utility and power applications, food/beverage/agriculture applications, freshness detection, fruit ripening control, fermentation process monitoring and control, flavor composition and identification, product quality and identification, refrigerant and fumigant detection, cosmetic/perfume applications, fragrance formulation, chemical/plastics/pharmaceuticals applications, fugitive emission identification, solvent recovery effectiveness, hospital/medical applications, anesthesia and sterilization gas detection, infectious disease detection, breath analysis and body fluids analysis.

Various other medical conditions and associated pathogens are set forth in picolines (see, Kostelc et al., *J. Periodont. Res.*, 15:185–192 (1981); Kostelc et al., *Clin. Chem.*, 27:842–845 (1981)). Overall, more than 80 volatile compounds have been shown to be associated with saliva or tongue scrapings (see, Claus etal., *J. High Resol. Chromatogr.*, 20:94–98 (1997)) and the

TABLE 1

INFECTIONS AND PATHOGENS

| Infection | Pathogen | Area of Interest |
|---|---|---|
| Acute Sinusitis | Strep. pneumoniae, H. flu, Moraxella catarrhalis, Group A strep., G(+) anaerobes, Staph. aureus | Sinus |
| Pharyngitis | Group A,C,G strep. | Pharynx |
| Pneumonia | Strep. pneumoniae, Mycoplasma, Chlamydia pneumoniae, H. flu | Lungs |
| Bronchitis | Strep. pneumoniae, H. Flu, Moraxella | Lungs |
| American Thoracic Society (ATS) Class III CAP Severe CAP ATS Class IV-ICU | Strep. pneumoniae, H. influenzae, Klebsiella, Staph. aureus, Legionella Sp., Pseudomonas aerug., other gram-negative bacteria; Strep. pneumoniae, Staph. aureus, Legionella Sp., Pseudomonas aerug., other gram negative bacteria | Lung |
| Cystitis in females; Pyelonephritis; Prostatitis or Epididymoorchitis | Enterobacteriaceae; Enterobacteriaceae & Enterococcus sp. | Urinary Tract |
| Acute Meningitis Meningitis(post surgical); Brain abscess | Hemophilus influenzae, Pneumococci, N. meningitidis Staphylococcus sp., gram-negative bacteria; Streptococcus sp., anaerobes, Staph. sp. | CNS |
| Biliary tract; Peritonitis or Diverticular abscess | Enterobacteriaceae, Enterococcus sp., anaerobes | Abdomen |
| Cellulitis; Lymphangitis Cat bite, Dog bite, Decubitus ulcers, (uncomplicated) or Diabetic foot ulcer (uncomplicated); Toxic Shock | Streptococcus sp., Staphylococcus sp.; Pasturella multicida, Staph & Strep., anaerobes, Gram negative bacteria; Gram-positive bacteria; Anaerobes | Skin |
| Endometritis/Endomyometritis Pelvic Inflammatory Disease; Septic Thrombophlebitis (postpartum) | Enterobacteriaceae, Chiamydia sp., Streptococcus sp. (group B Streptococcus), Neiserria gonorrhoeae | Pelvis |
| Endocarditis (IE) Prosthetic valve | Streptococci sp. Staphylococcus sp. Staphylococcus epi. | Heart |
| Septic arthritis, Prosthetic joint, Osteomyelitis | Staphylococcus sp. & Strep. sp., Neisseria gonorrhoeae, Staphylococcus sp., Staphylococcus sp., Staph & Strep.sp., Enterobacteriaceae, anaerobes | Bone & Joint |

G. Markers

As explained above, volatile sulfur compounds (e.g., $H_2S$, $CH_3-SH$, $CH_3-S-CH_3$) are the marker gases implicated in halitosis and periodontal diseases (see, Tonzetich, *Arch. Oral Biol*, 16:587–597 (1971); Rizzo, *Periodontics*, 5:233–236 (1967)). Other analytes that have been shown to correlate with such clinical findings include, but are not limited to, volatile organic acids (VOA), indole/skatole (indole), and diamines (see, Goldberg et al, *J. Dent. Res.*, 73:1168–1172 (1994); Goldberg et al., In Rosesberg M *Bad Breath Research Perspectives*, Ramat Publishing, Tel Aviv, pp. 71–85 (1995)).

In addition, several other analytes have been reported to be associated with oral infections including pyridines/ methods and apparatus of the present invention can be used to advantageously detect such marker compounds and gases.

Using the methods and apparatus of the present invention it is also possible to detect the off-gasses associated with bacteria associated with oral maladies including, but not limited to, *Prevotella intermedia; Fusobacterium nucleatum; Porphyromonas gingivalis; Porphyromonas endodontalis; Prevotella loescheii; Hemophilus parainfluenzae; Stomatococcus muci; Treponema denticola; Veillonella species; Peptostreptococcus anaerobius; Micros prevotii; Eubacterium limosum; Centipeda periodonti; Selemonad aremidis; Eubacterium species; Bacteriodes species; Fusobacterium periodonticum; Prevotella melaninogenica;*

*Klebsiella pneumoniae; Enterobacter cloacae;* Citrobacter species and *Stomatococcus mucilaginus.*

Moreover, a wide variety of analytes and fluids can be detected and analyzed using the disclosed sensors arrays and electronic noses so long as the subject analyte(s) and fluids are capable of generating a differential response across a plurality of sensors of the array. Analyte applications include broad ranges of chemical classes including, but not limited to, organics such as alkanes, alkenes, alkynes, dienes, alicyclic hydrocarbons, arenes, alcohols, ethers, ketones, aldehydes, carbonyls, carbanions, polynuclear aromatics and derivatives of such organics, e.g., halide derivatives, etc.; biomolecules such as sugars, isoprenes and isoprenoids; VOC; VOA; indoles; skatoles; diamines; pyridines; picolines; fatty acids; and derivatives of the forgoing, etc.

In addition to breath, the sensor arrays of the present invention can be used o identify various analytes in other biological fluids. These fluids include, but are not limited to, urine, perspiration, tears, blood, mucus, pus, salvia, feces, menstruation fluid, sperm, eggs, spinal fluid and mammary gland discharge.

In general, most conditions and diseases listed herein have microorganisms associated with them. The presence of marker gases and compounds associated with the microorganism is in turn, indicative of the presence of the disease or condition. In a preferred embodiment, the off-gas of the microorganism is the marker that is detected by methods and devices of the present invention.

III. ANESTHETICS

In certain anesthetic vaporizers, a carrier gas, such as air, oxygen or nitrous oxide, is divided between a first stream directed to a chamber, wherein an anesthetic liquid is resident and a second stream or bypass stream. The first and second streams are recombined before delivery to the patient. Another version of an anesthetic vaporizer is embodied in a device wherein the anesthetic agent is injected directly into the carrier gas stream.

In either instance, it is imperative that the concentration of volatile anesthetic liquid be known. The present invention provides methods and an apparatus for the process control of anesthetic gases. Using the methods and apparatus of the present invention, a fluid concentrator is optionally used when monitoring and quantitating anesthetic concentration.

By using the apparatus and sensors described herein, it is possible to detect and quantitate the concentration of volatile anesthetics including, but not limited to, halothane, isoflurane, servoflurane, desflurane and enflurane. As such, the present invention provides an anesthetic vaporizing system for quantitating the concentration of the anesthetic, comprising: a carrier gas source for delivering a carrier gas stream to a bypass valve, wherein the bypass valve splits the carrier gas stream into a first carrier gas stream for delivery to an inlet port and a second carrier gas stream for delivery to a joining valve;

a vaporizing chamber for an anesthetic agent, comprising the inlet port, an outlet port, a vaporizing means and a conduit for delivery of vaporized anesthetic from the outlet port to the joining valve; and an array of sensors in flow communication with the joining valve to quantitate the anesthetic. In preferred embodiments, the system further comprising a detector operatively associated with each sensor that provides a response in the presence of an anesthetic vapor.

Figure 4:
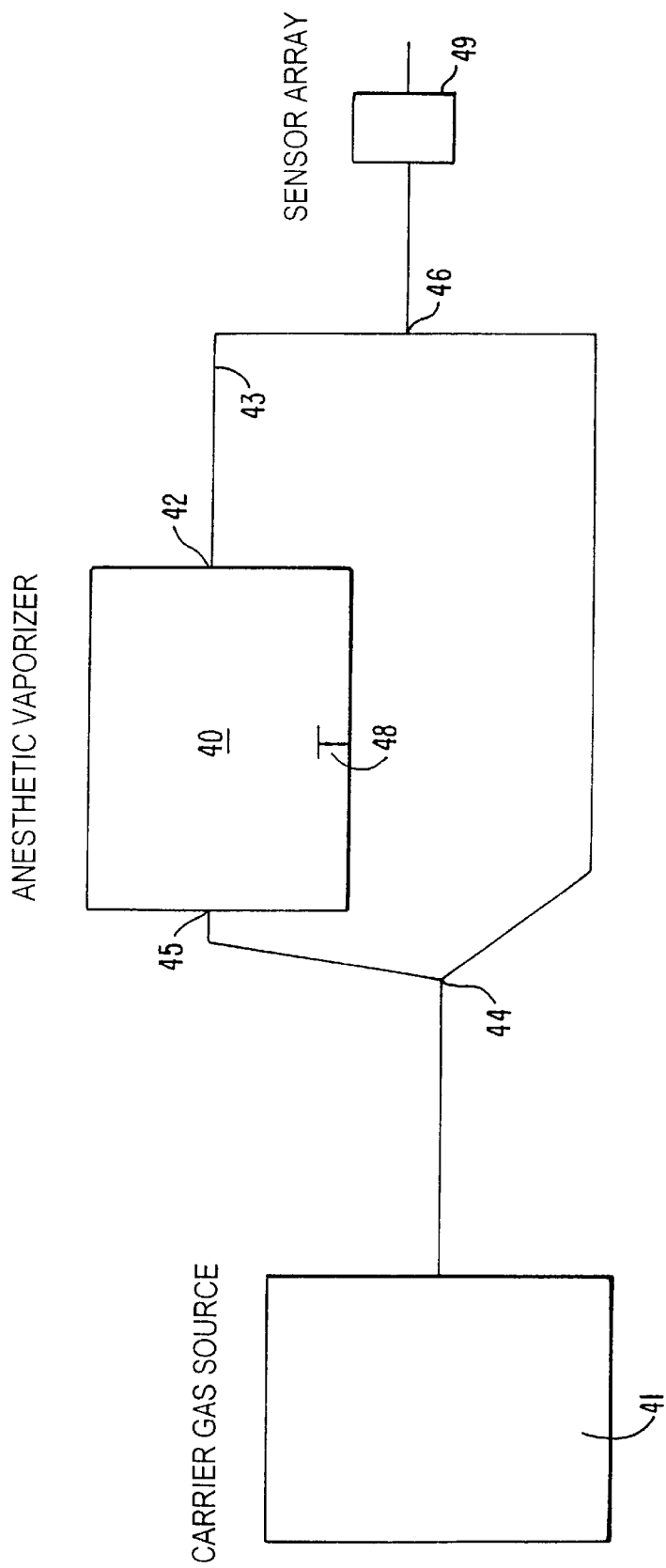
FIG. 4 is a block diagram of a vaporizing system of the present invention.

With reference to FIG. 4, the carrier gas source (41) delivers the carrier gas to a bypass valve (44), wherein the carrier gas is split between a first carrier gas stream for delivery to the inlet port (45) of the anesthetic vaporizer (40) and a second carrier gas stream which connects to a joining valve (46). The anesthetic vaporizer contains a vaporizing means, such as a heater, pressure souce or aspirator (48). The vaporizer includes an outlet port (42) for delivery of the vaporized anesthetic through a conduit (43) to the joining valve. The sensor array (49) is in flow communication with the joining valve.

The present invention also provides a method of quantitating an anesthetic vapor, comprising: containing the anesthetic vapor with a sensor array to produce a response; detecting the response with a detector, thereby quantitating the anesthetic vapor.

The following examples are meant to illustrate and not limit the present invention.

IV. EXAMPLES

Example 1

In this Example, the detection and identification of bacteria was conducted by measuring the metabolic products produced from plate bacteria cultures carried out using an electronic nose (a 32-sensor array) and a Fisher Linear Discrimination (FLD) algorithm.

As shown herein, the data was also examined using principal component analysis (PCA) and statistical isolinear multicategory analysis (SIMCA). The results carried out on two very distinct bacteria, i. e., *peptostreptococcus anerobius* and *porphyromonas gingivalis*, show that the two bacteria were clearly discriminated by the sensors as shown by PCA. The metabolites of additional an 11 bacteria and one fungus plus controls were tested and the data was examined using PCA, SIMCA and FLD and discrimination among the bacteria was demonstrated.

The objective of these experiments was to evaluate the discriminating capability of a thirty-two sensor array composed of mixtures of polymers and carbon black for metabolites produced by a variety of bacteria. Fourteen fresh cultures were tested for the 20 most commonly suspected malodor producing, oral and pharyngeal anaerobic and facultative bacteria including a fungus using a 32-sensor array. The experiment was done in two phases. The first phase consisted of testing two very distinct bacteria, *peptostreptococcus anerobius* and *porphyromonas gingivalis*, plus a control (the media in which the bacteria were independently grown). Four sample tubes of each bacterium and the control were tested to investigate reproducibility. The results from the first test indicated that *gingivalis* and *anerobius* could be discriminated from each other and the control using a sensor array discussed herein.

Ten samples of eleven bacteria, a fungus and ten controls were tested with the same sensor array used described above. Table 3 lists the bacteria plus the main metabolite known to be produced by these bacteria. Various statistical and mathematical techniques were used to analyze the data obtained with chemiresistors on these microorganisms. One of the methods used to classify the metabolites produced from the various bacteria was principal component analysis, an unsupervised pattern recognition technique. PCA transforms multidimensional data sets into a lower dimensional graphical representation, which describes a majority of the variation in a data set. PCA defines a new set of axes to plot the samples, they are constructed so that a maximum amount of variation is described with a minimum number of axes, and the data is hence readily visualized in this transformed data space (see, K. R. Beebe, R. J. Pell, M. B. Seasholtz, *Chemometrics: A Practical Guide*, Wiley, New York, 1998)

Another algorithm used to analyze the data set was Fisher Linear Discrimination (FLD). FLD seeks a linear combination of the variables, which maximizes the ratio of its between-group variance to its within-group variance (see, B. D. Ripley, *Pattern Recognition and Neural Networks*, University Press, Cambridge, 1996, Chapter 3, p 93).

Other algorithms used to analyze the data were K-nearest neighbor (KNN) and statistical isolinear multicategory analysis, SIMCA. Both of these algorithms are supervised pattern recognition methods used for predicting the class of unknown samples given a training set of samples with known class membership. With KNN, a classification is always made, whether or not the unknown is a member of the class in the training set. KNN is a much simpler algorithm than SIMCA because unlike SIMCA it makes no assumptions about the size or shape of the class. SIMCA can detect if an unknown sample is not a member of any class in the training set. SIMCA uses the shape and position of the object formed by the samples in a class for class definition (see, K. R. Beebe, R. J. Pell, M. B. Seasholtz, *Chemometrics: A Practical Guide*, Wiley, New York, 1998). The results obtained using all the described algorithms are set forth below.

A. EXPERIMENTAL

1. Testing Protocol

Thirty polymers were chosen based both on structural differences and on solubility to generate a thirty two sensor array. The testing protocol used for all the bacteria was the same and is described below. Anerobius and gingivalis were tested in one day, whereas the rest of the bacteria were tested over several days.

Testing instrument: A Keithley electrometer and scanner were used to scan the resistances of 32 sensors during the experiment.

Sampling: the headspace above the bacteria was sampled using nitrogen gas as the carrier. The flow rate used was 100 mL/minute. No dilution with air was done. The flow rate of the background air used to purge the sensors was 10 L/minute. No preconcentration was preformed.

Temperature: The temperature of the substrates was not controlled and the measurements were done at room temperature for the first phase study. The temperature of the substrates was maintained at 28±1° C. for the second phase study.

Purge and Exposure times: For each sample test, there were 60 seconds of background recording (purged with air), 120 seconds of exposure time, 120 seconds of recovery time (purged with air with RH level of about 3%), 180 seconds of recovery without recording the data (purged with air), and 30 seconds of final recording time (purged with air).

B. RESULTS AND DISCUSSION

1. Sensor Array Response

Figure 5A:
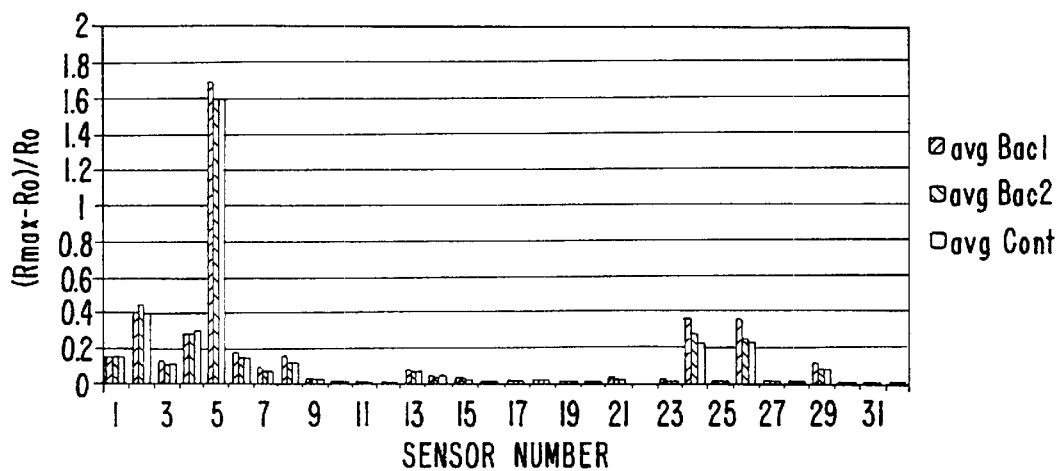
FIG. 5 illustrates various response patterns obtained using the devices of the present invention. Panel A illustrates the responses of 32 sensors to *anerobius* (Bac1), *gingivalis* (Bac2) and a control; Panel B illustrates responses of 32 sensors to *anerobius* (Bac1), *gingivalis* (Bac2) and a control (Expanded y- axis).
Figure 5B:
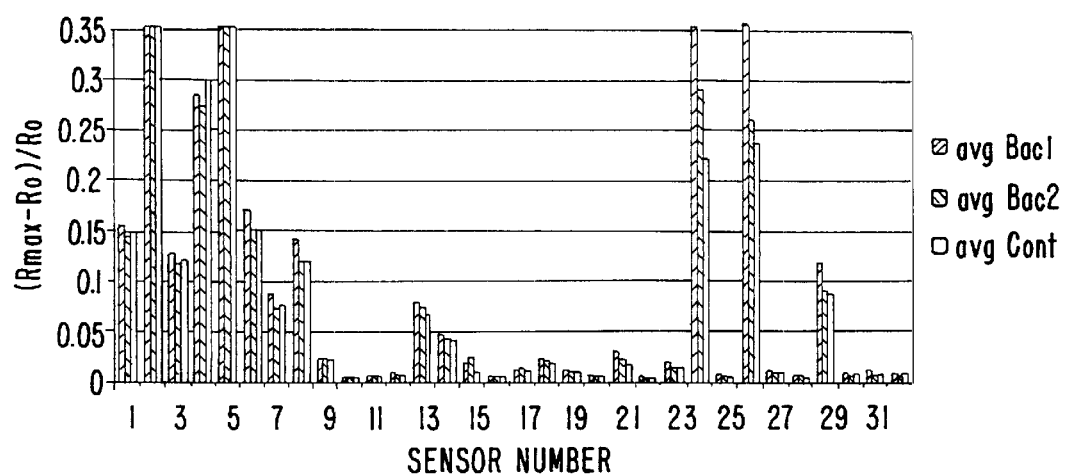
Figure 6:
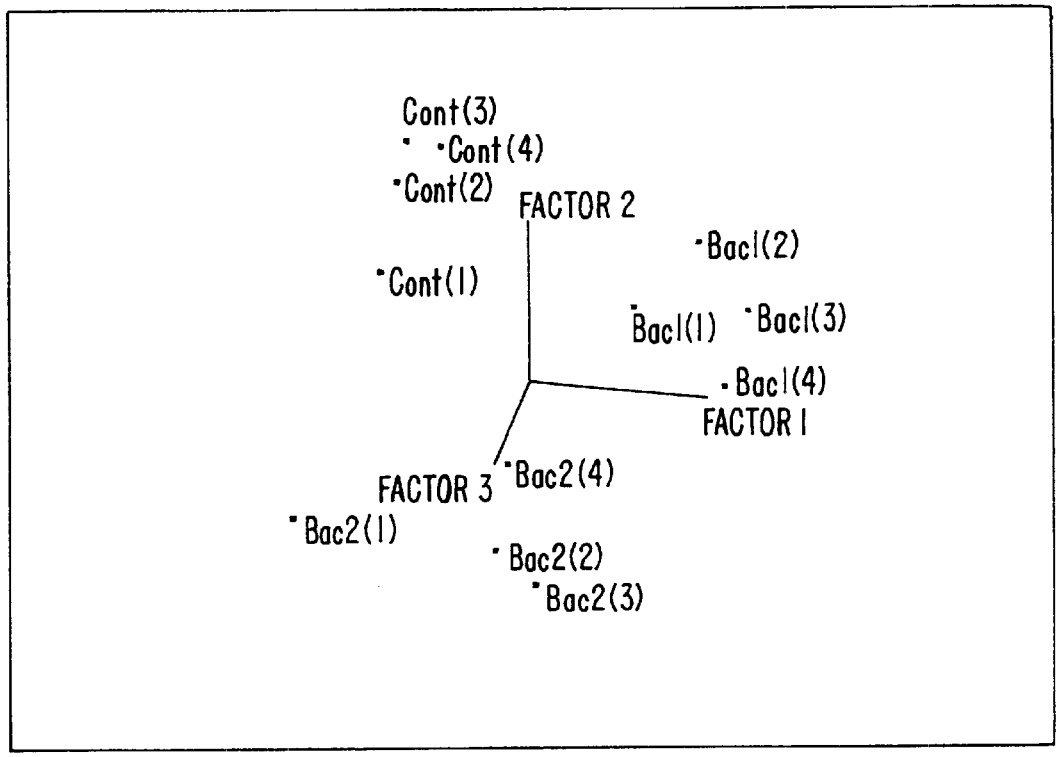
FIG. 6 illustrates the results of principle component analysis on a data set of *Ps anerobius* (Bac1) and *P gingivalis* bacteria (Bac2) plus the control (the medium in which the bacteria were grown).

The response pattern of the 32-sensor array described above to anerobius, gingivalis, and the control is shown in FIG. 5. Note that the reproducibility of the sensor array was very good. The response (the normalized resistance change, $(R_{max}-R_o)/R_o$), where $R_{max}$ and $R_o$ are the maximum and base (initial) resistance, respectively) of the sensor array to each sample tested is employed to form a covariance matrix, which is used to do principal component analysis. PCA of the two bacteria plus control (data not shown) were clearly discriminated by the sensor array. SIMCA was also used to evaluate the data. The model was built with all the data as the training set and the data from the first test was used as the unknown. A classification rate of 100% was obtained using the SIMCA algorithm. KNN was also used to examine the. data set. A model was built using the data from three sample tubes of each bacteria plus the control. One of the samples was used as the unknown. Using 3 or 5 nearest neighbors in the KNN algorithm gave a classification rate of 66%. The FLD algorithm was not used on this data set.

In the second phase study, ten samples of 11 bacteria and one fungus were tested. The temperature of the substrates was controlled at 28±0.1° C. for all tests. The sample tubes were not temperatures controlled. As described in the experimental section, each bacterium was tested 19 times among 9 test tubes. Thirty-two sensors responded to bacteria and one fungus, 19 times for each. A covariance matrix that contained 32 columns (one column for each sensor response) and 12×19 rows (bacteria tested at different times) was formed. This matrix was used to do principal component analysis.

A different algorithm, Fisher Linear Discrimination, was introduced to process the data set. To construct a model using the FLD method, it is required that the data take the form of a square matrix. The columns and rows in the matrix correspond to the number of sensors and the number of test samples, respectively. Hence, to use FLD, the number of sensors needs to be equal to the number of sample tests. Each of the 11 bacteria and one fungus were tested 19 times thus, only 19 sensors could be used to construct the FLD model. Hence, a square matrix was formed using each of the bacteria tested 19 times and choosing 19 sensors out of the 32. The very first test (tube 1) and the last test (tube 5) of each bacterium were used as unknowns. The first 19 sensors out of the 32-sensor array were found to give the highest prediction rate out of other sensor combinations. Twenty-four unknowns were predicted from the FLD model. The results provided a classification rate of 91.7% (see, Gibson, T. D., Prosser, O., Hulbert, J. N., Marshall, R. W., Corcoran, P., Lowery, P., Ruck-Keene, E. A., Heron, S., *Sensors and Actuators* (B) 44, 413–422, 1997).

As a comparison, a SIMCA model was built with the same training set used for the FLD analysis. The same 24 unknowns was used for SIMCA prediction. The results provided a classification rate of 75%. The KKN algorithm was also used and the classification rate was 66%.

TABLE 2

SENSOR COMPOSITION AND DEPOSITION CONDITIONS

| P'er # | Polymer | Sensor # | Solvent | Dilution Ratio |
|---|---|---|---|---|
| CHIP ENX-1-070798 | | | | |
| 19 | Hydroxypropyl cellulose | Sr 1 | water | 150 to 1 |
| 22 | Methyl vinyl ether-co-maleic acid, 50/50 | Sr 2 | water | 151 to 1 |
| 34 | Polyacrylamide | Sr 3 | water | 150 to 1 |
| 35 | Polyacrylamide, carboxyl modified (LC) | Sr 4 | water | 150 to 1 |
| 36 | Polyacrylamide, carboxyl modified (HG) | Sr 5 | water | 150 to 1 |

TABLE 2-continued

SENSOR COMPOSITION AND DEPOSITION CONDITIONS

| P'er # | Polymer | Sensor # | Solvent | Dilution Ratio |
|---|---|---|---|---|
| 55 | Poly(ethylene oxide) | Sr 6 | water | 150 to 1 |
| 73 | Poly(vinyl alcohol), 100% hydrolyzed | Sr 7 | water | 150 to 1 |
| 74 | Poly(vinyl alcohol), 98% hydrolyzed | Sr 8 | water | 150 to 1 |
| | CHIP ENX-2-070798 | | | |
| 3 | Alginic acid, sodium salt | Sr 9 | toluene | 25 to 1 |
| 10 | Ethylene-co-ethyl acrylate, 82/18 | Sr 10 | toluene | 25 to 1 |
| 12 | Ethylene-co-vinyl acetate, 86/14 | Sr 11 | toluene | 25 to 1 |
| 39 | 1,2-Polybutadiene | Sr 12 | toluene | 25 to 1 |
| 42 | Polycaprolactone | Sr 13 | toluene | 25 to 1 |
| 41 | Poly(n-butyl methacrylate) | Sr 14 | toluene | 25 to 1 |
| 48 | Poly(n-ethyl methacrylate) | Sr 15 | toluene | 25 to 1 |
| 50 | Polyethylene, chlorinated (42& Cl) | Sr 16 | toluene | 25 to 1 |
| | CHIP ENX-3-070798 | | | |
| 54 | Polyethylene, chlorosulfonated | Sr 17 | toluene | 25 to 1 |
| 59 | Poly(isobutyl methacrylate) | Sr 18 | toluene | 25 to 1 |
| 63 | Poly(α-methyl styrene) | Sr 19 | toluene | 25 to 1 |
| 68 | Polystyrene | Sr 20 | toluene | 25 to 1 |
| 80 | Poly(vinyl stearate) | Sr 21 | toluene | 25 to 1 |
| 87 | Styrene/ethylene/butylene, ABA block | Sr 22 | toluene | 25 to 1 |
| 95 | Vinyl chloride/vinyl acetate/hydroxypropyl | Sr 23 | toluene | 25 to 1 |
| 79 | Poly(vinyl pyrrolidone) | Sr 24 | water | 150 to 1 |
| | CHIP ENX-4-070798 | | | |
| 63 | Poly(α-methyl styrene) | Sr 25 | toluene | 25 to 1 |
| 79 | Poly(vinyl pyrrolidone) | Sr 26 | water | 150 to 1 |
| 86 | Styrene-co-butyl methacrylate | Sr 27 | toluene | 25 to 1 |
| 82 | Styrene-co-acrylonitryle, 75/25 | Sr 28 | THF | 100 to 1 |
| 90 | Vinyl alcohol-co-vinyl butyral; 20/80 | Sr 29 | THF | 100 to 1 |
| 104 | Poly (4-methoxy styrene) | Sr 30 | THF | 100 to 1 |
| 105 | Poly methyl hydrosiloxane | Sr 31 | THF | 100 to 1 |
| 102 | Poly diphenoxyphosphazene | Sr 32 | THF | 100 to 1 | carbon black was used in each sensor at a concentration between 20–25 wt %

TABLE 3

LIST OF BACTERIA AND THEIR METABOLIC PRODUCTS

| BACTERIA | NOMENCLATURE | METABOLIC PRODUCTS OR OFF-GASES |
|---|---|---|
| *Enterobacter cloacae* | Bac 1 | Isobutyric and isovaleric acid |
| *Cit. Koseri* | Bac 2 | N/A |
| *Psuedomonas Aeruginosa* | Bac 3 | N/A |
| *Veilonella species* | Bac 4 | Acetic and propionic acid and isoamyl alcohol |
| *Prevotella melaninogenica* | Bac 5 | Isovaleric acid |
| *Escherichia coli* | Bac 6 | Acetic and propionic acid |
| *Kiebseilla Pneumoniae* | Bac 7 | Methyl ethyl ketone, methylbutanal, 2-butanol, pentanone, dimethyl sulfide, isobutanol, isopentylacetate, 2-heptanone isopentanol, 2-nonanone, 2-undecanone |
| *Streptococcus mutans* | Bac 8 | Acetic acid, propionic acid |
| *Candida albicans* | Bac 9 | N/A |
| *Prevotella intermedia* | Bac 10 | Isovaleric acid |
| *Fusobacterium nucleatum* | Bac 11 | Acetic, propionic and butyric acid |
| *Staph. aureus* | Bac 12 | Acetic, 2-butanone, 2-butanol, pentanone, methyl butanal, toluene, 2-heptanone, isopentanol, 2-nonanone, 2-undecanone, acetone, 2-nondecagon |
| *Peptostreptococcus anerobius* | | Acetic, isobutyric, butyric, isovaleric and isocaproic acid |
| *Porphyromonas gingivalis* | | Isovaleric acid |

*This is a fungus

Example 2

This Example illustrates that the apparatus and methods comprising the sensor arrays of the present invention are suitable for process control of anesthetic gases. As disclosed herein, a method for monitoring anesthetic gases in order to establish reliable monitoring of a patient's condition while under anesthetics is possible. Conducting-polymer composite sensors change resistance when exposed to an analyte in the vapor phase, and the pattern of such resistance changes across an array allows identification of a concentration of an analyte. The pattern height allows identification of the concentration of an analyte. The experiments show that these arrays are suitable for process control over the concentration of anesthetic gases at levels that are clinically of interest.

Figure 7:
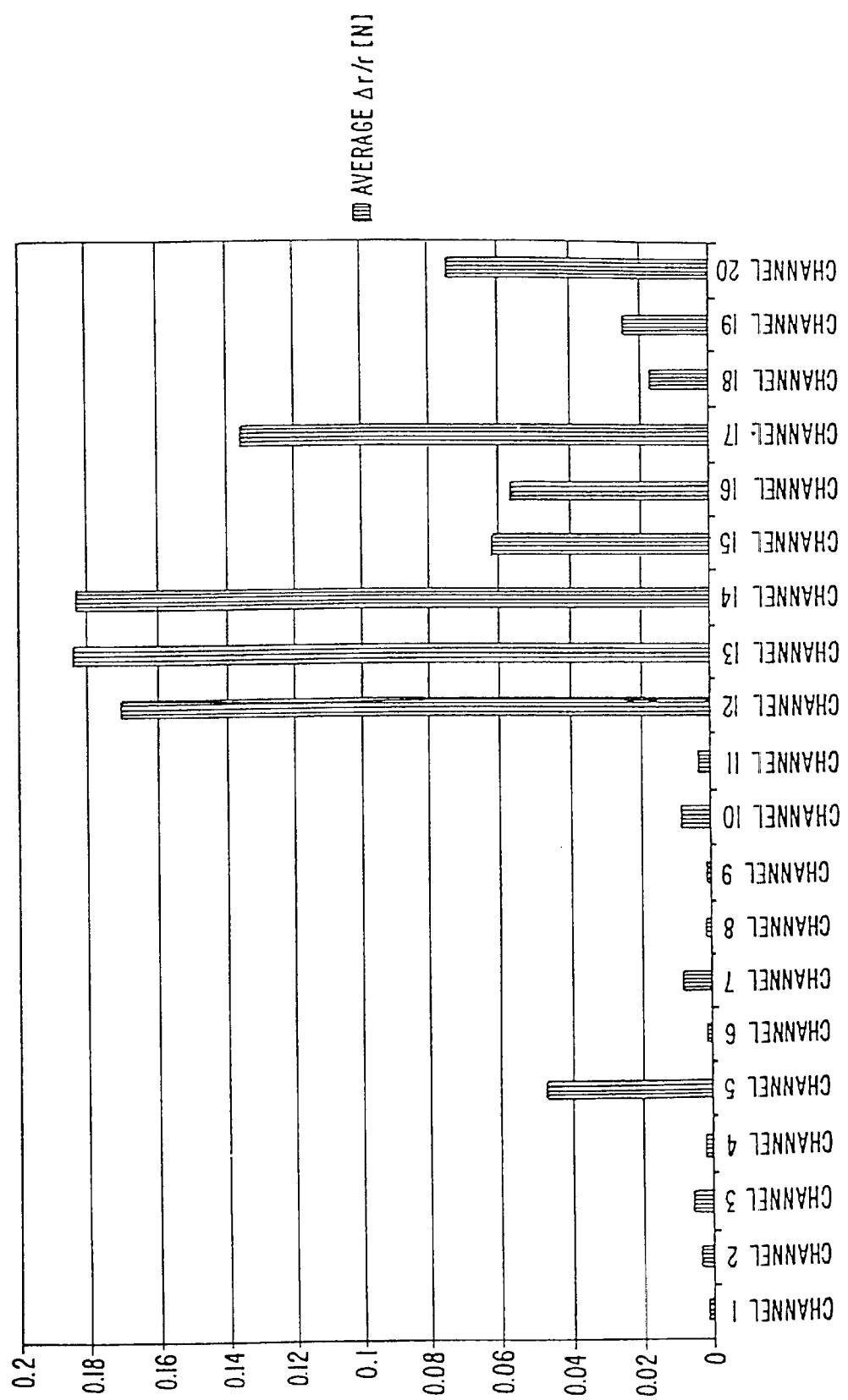
FIG. 7 illustrates the response of sensors in the presence of 3 percent halothane.
Figure 8:
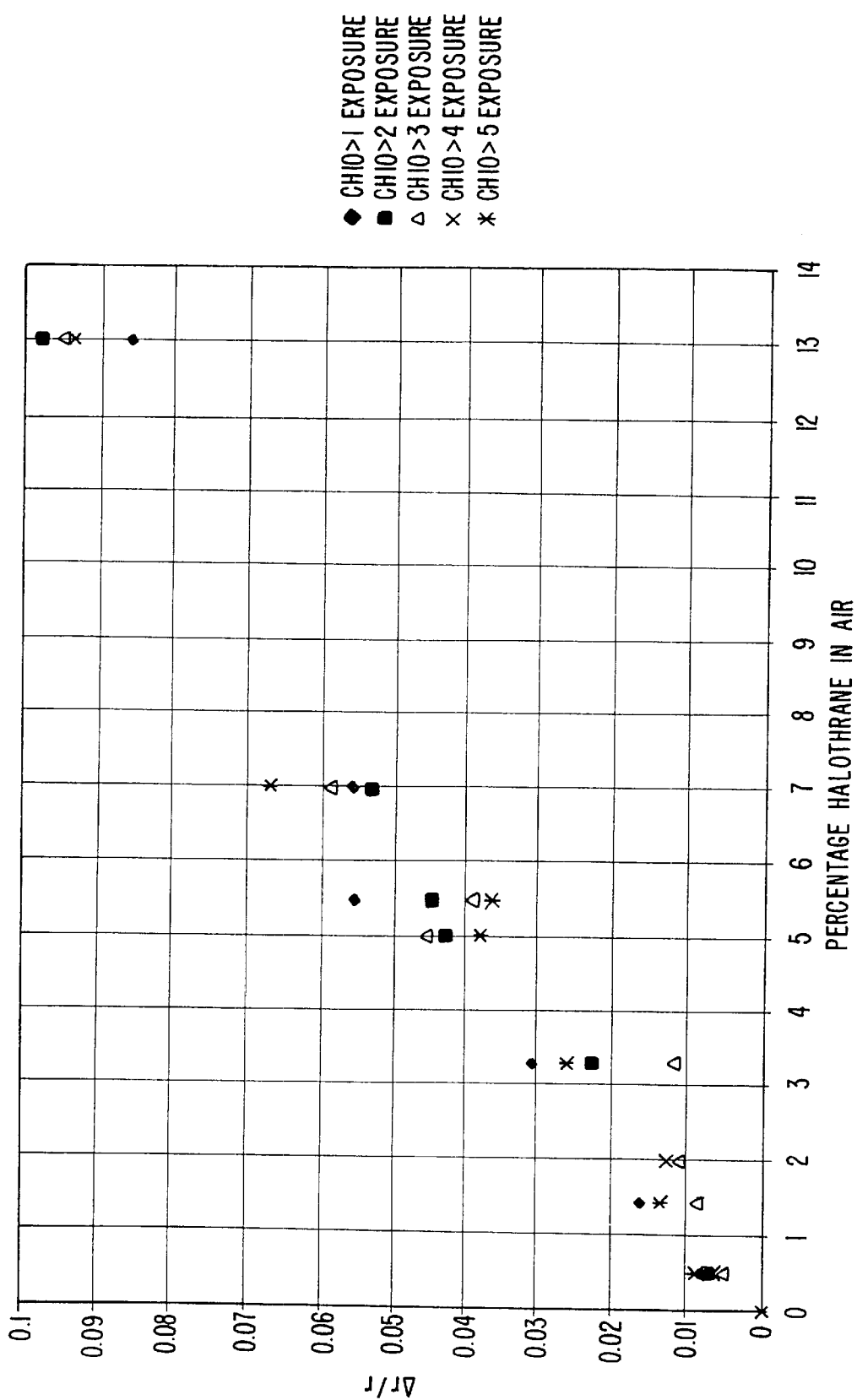
FIG. 8 illustrates the results of the response of sensor array in the presence of halothane.

Using a 18-sensor array a suitable concentration of halothane was delivered. The flow rate of the carbon dioxide carrier gas was 10 mL/min. The anesthetic gas flow rate was 0.2 mL/min, thus the ratio of carrier gas flow over the summation of the carrier gas flow and the anesthetic gas flow was 2%. FIG. 7 illustrates the response of 2% halothane on the sensor array. FIG. 8 illustrates the linear response for sensor 10 with halothane concentration.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes in their entirety.

What is claimed is:

1. A device for detecting the presence of an analyte, wherein said analyte is a microorganism marker gas indicative of a respiratory tract infection, said device comprising:
    a) a sample chamber having a fluid inlet port for the influx of said analyte;
    b) a fluid concentrator in flow communication with said sample chamber, said fluid concentrator having an absorbent material capable of absorbing said analyte and capable of desorbing a concentrated analyte; and
    c) an array of sensors in fluid communication with said concentrated analyte.

2. The device according to 1, claim further comprising a detector operatively associated with each sensor and providing a response in the presence of said analyte.

3. A device in accordance with claim 1, wherein said fluid concentrator is disposed within said sample chamber.

4. A device in accordance with claim 1, wherein said sensor array is disposed within said sample chamber.

5. A device in accordance with claim 1, wherein said fluid concentrator and said sensor array are disposed within said sample chamber.

6. A device in accordance with claim 5, further comprising a means to flow said analyte fluid from said inlet port to said fluid concentrator and to said sensor array.

7. A device in accordance with claim 1, wherein said sample chamber comprises an internally controlled atmosphere.

8. A device in accordance with claim 1, wherein said absorbent material is a member selected from the group consisting of a nanoporous material, a microporous material, a nonporous material and combinations thereof.

9. A device in accordance with claim 8, wherein said absorbent material is a member selected from the group consisting of activated carbon, silica gel, activated alumina, molecular sieve carbon, molecular sieve zeolites, silicalite, $AlPO_4$, a polymer, a co-polymer, alumina and mixtures thereof.

10. A device in accordance with claim 8, wherein said absorbent has a pore size from about 1 nm to about 100 nm.

11. A device in accordance with claim 10, wherein said absorbent has a pore size from about 1 nm to about 50 nm.

12. A device in accordance with claim 1, wherein said concentrated analyte is desorbed using a member selected from the group consisting of heating, purging, stripping, pressuring or a combination thereof.

13. A device in accordance with claim 1, further comprising an additional adsorbent to remove unwanted material from said analyte fluid.

14. A device in accordance with claim 13, wherein said unwanted material is a gas contaminate.

15. A device in accordance with claim 13, wherein said unwanted material is moisture.

16. A device in accordance with claim 1, wherein said response is an electrical response, and wherein said electrical response is a member selected from the group consisting of electrical resistance, impedance and capacitance.

17. A device in accordance with claim 1, wherein said array of sensors comprises a member selected from the group consisting of a surface acoustic wave sensor, a quartz microbalance sensor; a conductive composite; a chemiresistor; a metal oxide gas sensor and a conducting polymer sensor, a dye-impregnated polymer film on fiber optic detector, a polymer-coated micromirror, an electrochemical gas detector, a chemically sensitive field-effect transistor, a carbon black-polymer composite, a micro-electro-mechanical system device and a micro-opto-electro-mechanical system device.

18. A device in accordance with claim 1, wherein said analyte is a member selected from the group consisting of alkanes, alkenes, alkynes, dienes, alicyclic hydrocarbons, arenes, alcohols, ethers, ketones, aldehydes, carbonyls, carbanions, polynuclear aromatics, heterocycles, organic derivatives, biomolecules, microorganisms, fingi, bacteria, microbes, viruses, metabolites, sugars, isoprenes and isoprenoids, fatty acids and their derivatives.

19. A device in accordance with claim 1, wherein said device is used in an application selected from the group consisting of environmental toxicology, remediation, biomedicine, material quality control, food monitoring, agricultural monitoring, heavy industrial manufacturing, ambient air monitoring, worker protection, emissions control, product quality testing, oil/gas petrochemical applications, combustible gas detection, $H_2S$ monitoring, hazardous leak detection, emergency response and law enforcement applications, explosives detection, utility and power applications, food/beverage/agriculture applications, freshness detection, fruit ripening control, fermentation process monitoring and control, flavor composition and identification, product quality and identification, refrigerant and fumigant detection, cosmetic/perfume applications, fragrance formulation, chemical/plastics/pharmaceuticals applications, fugitive emission identification, solvent recovery effectiveness, hospital/medical applications, anesthesia and sterilization gas detection, infectious disease detection, breath analysis and body fluids analysis.

20. A device in accordance with claim 1, further comprising robotic armature for high throughput assay screening.

21. A device in accordance with claim 1, wherein said array of sensors comprise about 10 to about 100 sensors.

22. A device in accordance with claim 1, wherein said array of sensors comprise about 100 to about 1000 sensors.

23. A device in accordance with claim 1, wherein said array of sensors comprise about 1000 to about $10^6$ sensors.

24. A device in accordance with claim 1, wherein at least two sensors are compositionally different.

25. A device in accordance with claim 1, further comprising a computer, response profiles and an algorithm.

26. A device in accordance with claim 25, wherein said algorithm is a pattern recognition algorithm.

27. A device in accordance with claim 25, further comprising a neural network for software or hardware analysis.

28. A device in accordance with claim 1, wherein said device is a handheld device.

29. The device in accordance with claim 1, wherein said respiratory tract infection is a lower respiratory tract infection.

30. The device in accordance with claim 1, wherein said respiratory tract infection is an upper respiratory tract infection.

31. The device in accordance with claim 29, wherein said lower respiratory tract infection is selected from pneumonia or bronchitis.

32. The device in accordance with claim 30, wherein said upper respiratory tract infection is selected from sinusitis or pharyngitis.

33. A device for detecting a respiratory tract infection by detecting an indicative marker gas, said device comprising:
- a) a sample chamber having a fluid inlet port for the influx of said marker gas;
- b) a fluid concentrator in flow communication with said sample chamber, said fluid concentrator having an absorbent material capable of absorbing said marker gas and capable of desorbing a concentrated marker gas; and
- c) an array of sensors in fluid communication with said concentrated marker gas.

34. The device in accordance with claim 33, wherein said respiratory tract infection is a lower respiratory tract infection.

35. The device in accordance with claim 33, wherein said respiratory tract infection is an upper respiratory tract infection.

36. The device in accordance with claim 34, wherein said lower respiratory tract infection is selected from pneumonia or bronchitis.

37. The device in accordance with claim 34, wherein said upper respiratory tract infection is selected from sinusitis or pharyngitis.

38. A device for detecting a urinary tract infection by detecting an indicative marker gas, said device comprising:
- a) a sample chamber having a fluid inlet port for the influx of said indicative marker gas;
- b) a fluid concentrator in flow communication with said sample chamber, said fluid concentrator having an absorbent material capable of absorbing said indicative marker gas and capable of desorbing a concentrated indicative marker gas; and
- c) an array of sensors in fluid communication with said concentrated indicative marker gas.

39. The device in accordance with claim 38, wherein said indicative marker gas is a microorganism off gas selected from Enterobacteriaceae, Enterococcus sp. and combinations thereof.

40. A device for detecting bacterial vaginitis by detecting an indicative marker gas, said device comprising:
- a) a sample chamber having a fluid inlet port for the influx of said indicative marker gas;
- b) a fluid concentrator in flow communication with said sample chamber, said fluid concentrator having an absorbent material capable of absorbing said indicative marker gas and capable of desorbing a concentrated indicative marker gas; and
- c) an array of sensors in fluid communication with said concentrated indicative marker gas.

41. The device in accordance with claim 40, wherein said indicative marker gas is selected from the group consisting of methylamine, isobutylamine, putrescine, cadaverine, histamine, tyramine, and phenethylamine.

42. A device for detecting the presence of an analyte, wherein said analyte is a microorganism marker gas indicative of a urinary tract infection said device comprising:
- a) a sample chamber having a fluid inlet port for the influx of said indicative marker gas;
- b) a fluid concentrator in flow communication with said sample chamber, said fluid concentrator having an absorbent material capable of absorbing said indicative marker gas and capable of desorbing a concentrated indicative marker gas; and
- c) an array of sensors in fluid communication with said concentrated indicative marker gas.

43. The device in accordance with claim 42, wherein said indicative marker gas is an off gas from Enterobacteriaceae, Enterococcus sp. and combinations thereof.

44. A device for detecting the presence of an analyte, wherein said analyte is a marker gas indicative of bacterial vaginitis, said device comprising:
- a) a sample chamber having a fluid inlet port for the influx of said indicative marker gas;
- b) a fluid concentrator in flow communication with said sample chamber, said fluid concentrator having an absorbent material capable of absorbing said indicative marker gas and capable of desorbing a concentrated indicative marker gas; and
- c) an array of sensors in fluid communication with said concentrated indicative marker gas.

45. The device in accordance with claim 44, wherein said indicative marker gas is selected from the group consisting of methylamine, isobutylamine, putrescine, cadaverine, histamine, tyramine, and phenethylamine.

* * * * *